United States Patent [19]

Dressler

[11] Patent Number: 4,599,464
[45] Date of Patent: Jul. 8, 1986

[54] NOVEL COMPOSITIONS

[75] Inventor: Hans Dressler, Monroeville, Pa.

[73] Assignee: Koppers Company, Inc., Pittsburgh, Pa.

[21] Appl. No.: 788,731

[22] Filed: Oct. 17, 1985

[51] Int. Cl.$^4$ .............................................. C07C 39/12
[52] U.S. Cl. .................................. 568/766; 568/733; 568/744
[58] Field of Search ................ 568/733, 766, 744, 731

[56] References Cited

U.S. PATENT DOCUMENTS 3,972,951  8/1976  Filbey et al. .................. 568/744
4,514,577  4/1985  Filbey et al. .................. 568/744

*Primary Examiner*—Werren B. Lone
*Attorney, Agent, or Firm*—Donald M. MacKay; Herbert J. Zeh, Jr.

[57] ABSTRACT

Novel compositions useful as antioxidants are formed by the reaction of resorcinol with an alkenylbenzene.

10 Claims, No Drawings

NOVEL COMPOSITIONS

BRIEF DESCRIPTION OF THE INVENTION

This invention relates to novel compositions formed by the reaction of resorcinol with an alkenylbenzene useful as antioxidants and heat (process) stabilizers which are represented by the structural formula:

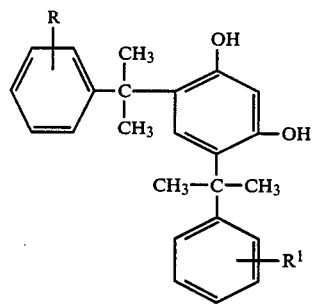

wherein R and $R^1$ are the same or different and are selected from hydrogen, methyl, ethyl and propyl or isopropyl.

DETAILED DESCRIPTION OF THE INVENTION

The novel compositions are made by the acid-catalyzed alkylation of resorcinol with isopropenylbenzene, and o-, m-, or p- methyl, ethyl or (iso) propyl-isopropenylbenzene. The procedure is illustrated by the following example with the preparation of 4,6-di-(alpha, alpha-dimethylbenzyl) resorcinol (alternatively referred to herein as DMBR).

EXAMPLE 1

To a slurry of 110.0 g resorcinol, 3.3 g of TX acid (a mixture of toluene-sulfonic acid and xylenesulfonic acid made by Nease Chemical Co.) and 600 ml. of n-heptane was added with stirring at 65° C. during 1.5 hrs. 264.0 g of isopropenylbenzene (98%). The mixture was then held at 65° C. for another 1 hr. and at 75° C. for 3 hrs. To the resulting thick slurry was added a solution of 1.3 g of sodium hydroxide in 5 ml. of water with stirring. The charge was cooled to 25° C. and filtered. The filter cake was washed four times with 100 ml. of fresh water, then washed with two 100 ml. portions of n-heptane and vacuum-dried at 100° C./25 Torr to give 320 g (92.5% yield) of light-grey 4,6-di($\alpha,\alpha$-dimethylbenzyl) resorcinol, m.p. 130.4° C.; after recrystallization from toluene the product was colorless, m.p. 135.9° C. The structure was confirmed by IR/NMR spectroscopic analyses.

The alkenylbenzene and resorcinol can be reacted in a mole ratio of from 1.5-2.5 to 1 but preferably from 1.9-2.2 to 1. A solvent is not required but is preferred. Suitable solvents include aliphatic and aromatic hydrocarbons and halogenated hydrocarbons but the aromatic hydrocarbons are preferred. Acid catalysts which can be employed are e.g., mineral acids such as hydrochloric and sulfuric acid, acid washed clays, and strong organic acids such as the sulfonic acids and sulfonic acid-type ion-exchange resins in an amount between about 0.01% and about 5.0 mole percent based on resorcinol, but 0.5-2.0 mole percent is preferred.

Reaction temperatures can be between about 30° C. and about 130° C. but are preferably between about 50° C. and about 100° C. Reaction times are generally between about one and about five hours, depending on the temperature and amount of catalyst used.

The resultant slurry is treated with an amount of a base at least sufficient to neutralize the acid catalyst, the product is filtered and the filter cake washed several times, first with water and then a solvent, and then dried to a constant weight and finally recrystallized from a suitable solvent, if the highest purity is desired.

By thermogravimetric analysis (TGA) at a heating rate of 20° C./min. in a flow of nitrogen, DMBR undergoes initial weight loss at ca. 204° C. and reaches 50% weight loss at 315° C. This is similar to the weight loss of the commercial antioxidant 4,4'-thio-bis-3-methyl-6-t-butylphenol with an initial weight loss at ca. 195° C. and 50% weight loss at ca. 310° C. under the same conditions.

EXAMPLE 2

DMBR was incorporated into high density polyethylene at a concentration of 0.15 wt. % on a Brabender mill and then aged in an oven at 130° C. in air for 120 hrs. to failure. An unstabilized control failed at 50 hrs.

EXAMPLE 3

DMBR (0.15 wt. %) in high density polyethylene was processed on a Brabender mill at 260° C./80 rpm for 15 min., and the melt index compared with the initial melt index. There was a 41% decrease. A comparison with a high density polyethylene composition containing 0.15% Irganox 1010 showed an 88% decrease. Thus, DMBR is an excellent process stabilizer for polyethylene.

EXAMPLE 4

DMBR was evaluated as an antioxidant in Sunvis 21 paraffinic oil base stock for engine lubricants at a concentration of 0.5 wt. % at a temperature of 350° F. with dry air passed through at a rate of 60 ml/minute. It took 324 hours for the oil to gel, indicating that DMBR is a very good high-temperature antioxidant for lubricants. Without an antioxidant additive the Sunvis 21 oil gelled after 132 hrs. at 350° F.

EXAMPLE 5

DMBR was evaluated as a biocide and required only 50 ppm to inhibit growth of Bacillus subtilis and 100 ppm to inhibit growth of Staphylococcus aureus.

EXAMPLE 6

A natural rubber formulation with 2 phr DMBR was prepared and tested compared with a rubber of the same formulation but without DMBR. The formulations and properties were as follows:

| Ingredients | | Comparison Without Antioxidant |
|---|---|---|
| DMBR AS ANTIOXIDANT IN RUBBER | | |

| | -continued | |
|---|---|---|
| Smoked Sheet Rubber | 100 | 100 |
| Stearic Acid | 2 | 2 |
| Zinc Oxide | 5 | 5 |
| TiO$_2$ | 20 | 20 |
| Dixie Clay | 50 | 50 |
| Atomite - filter whitener (calcium carbonate) | 50 | 50 |
| Reogen - paraffin oil/sulfonate blend (plasticizer, processing acid) | 2 | 2 |
| Altax - Benzothiazil disulfide (accelerator) | 1 | 1 |
| Methyl Tuads - Tetramethylthiuram disulfide (accelerator) | .1 | .1 |
| Sulfur | 2.75 | 2.75 |
| DMBR | 2 | 2 |

| | With DMBR | Without DMBR |
|---|---|---|
| PHYSICAL PROPERTIES | | |
| Press cures at 153° C.(307° F.) Cured: 10 Minutes | | |
| 300% Modulus, psi | 760 | 800 |
| Tensile, psi | 2440 | 2340 |
| % Elongation | 600 | 570 |
| Hardness | 58 | 58 |
| AFTER AGING 2 DAYS IN TEST TUBES AT 100° C.(212° F.) | | |
| Tensile, % Retained | 57 | 22 |
| Elongation % Retained | 73 | 47 |
| Hardness, Points Changed | +4 | +1 |
| AFTER AGING 4 DAYS IN TEST TUBES AT 100° C.(212° F.) | | |
| Tensile, % Retained | 34 | 14 |
| Elongation, % Retained | 58 | 14 |
| Hardness, Points Changed | +3 | +3 |
| REHOMETER AT 153° C.(307° F.) 30 Minute Motor, 60 Second Preheat, 100 Range, 3° Arc | | |
| Maximum Torque | 55.8 | 59 |
| Minimum Torque | 15.8 | 15 |
| T90, minutes | 9.5 | 8.8 |
| T2, minutes | 4 | 3.5 |
| DISCOLORATION OF COMPOUND | | |
| Uncured | Off White | Off White |
| Cured | " | " |
| DISCOLORATION AFTER 24 HOURS UNDER RS LAMP AT 38° C.(100° F.) G.E. BRIGHTNESS | | |
| Press cures 10 minutes at 153° C.(307° F.) | | |
| Unexposed | 55.2 | 55.7 |
| Exposed 24 hours | 19.8 | 19.3 |

These data show that the formulation with DMBR gave much improvment in heat resistance over the formulation without antioxidant.

EXAMPLE 7

In accordance with the general procedures of the above examples 4,6-di-(4',alpha,alpha-trimethylbenzyl) resorcinol, 4,6-di-(4'-ethyl-alpha,alpha-dimethylbenzyl) resorcinol, and 4,6-di-(3'-isopropyl-alpha,alpha-dimethylbenzyl) resorcinol are prepared and tested with similar results.

The compositions of the invention are used in minor amounts as can be seen from the above examples with DMBR. In a plastic such as polyethylene, from 0.01 to 1.0% is generally sufficient, in a lubricant from 0.5 to 5.0% is generally sufficient, in a rubber, from 0.5 to 5.0 phr is generally sufficient and in a biocide generally from 50 to 100 ppm is sufficient.

While the above description illustrates the Best Mode and preferred embodiments of the invention, it should be understood that one may make variations obvious to one of ordinary skill which are within the concepts of this invention. Accordingly, it is intended that the invention be limited only by the appended claims.

What is claimed is:

1. Compositions of the formula:

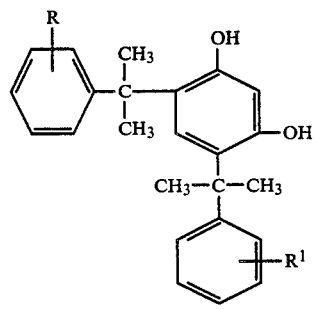

wherein R and R$^1$ are the same or different and are selected from the group consisting of hydrogen, methyl, ethyl, propyl and isopropyl.

2. A composition of claim 1 wherein R and R$^1$ are hydrogen.

3. The composition of claim 1 wherein R and R$^1$ are methyl.

4. The composition of claim 1 wherein R and R$^1$ are ethyl.

5. The composition of claim 1 wherein R and R$^1$ are (iso)propyl.

6. The composition of claim 1 wherein R is H and R$^1$ is an alkyl.

7. An organic material subject to deterioration by heat and/or oxidation stabilized by addition of a minor but effective amount of a composition of claim 1.

8. The material of claim 7 wherein R and R$^1$ are hydrogen.

9. A method of inhibiting the growth of bacteria comprising applying to said bacteria a biocidal amount of a composition of claim 1.

10. The method of claim 9 wherein R and R$^1$ are hydrogen.

* * * * *